United States Patent [19]

Vogel et al.

[11] Patent Number: 4,595,783
[45] Date of Patent: Jun. 17, 1986

[54] MAGNESIUM CHLORIDE OR PHOSPHONIUM HALIDE DERIVATIVES OF 3,7,11-TRIMETHYL-DODECA-2,6(10)-DIENE(TRIENE)-1-OL

[76] Inventors: Friedrich Vogel, 35 Oak La., Mountain Lake, N.J. 07026; Joachim Paust, Ringstr. 3, 6708 Neuhofen; Axel Nuerrenbach, Koenigsberger Str. 7, 6718 Gruenstadt, both of Fed. Rep. of Germany

[21] Appl. No.: 646,271

[22] Filed: Aug. 31, 1984

Related U.S. Application Data

[62] Division of Ser. No. 508,802, Jun. 28, 1983, Pat. No. 4,544,758.

[30] Foreign Application Priority Data

Jun. 29, 1982 [DE] Fed. Rep. of Germany ....... 3224108

[51] Int. Cl.[4] .............................. C07F 9/54; C07F 3/02
[52] U.S. Cl. ................................... 568/9; 260/665 G; 558/217
[58] Field of Search ................ 260/956, 665 G; 568/9

[56] References Cited

U.S. PATENT DOCUMENTS 3,342,877  9/1967  Julia ............................... 260/665 G
3,669,996  6/1972  Siddall et al. ........................ 260/956

Primary Examiner—Anton H. Sutto
Attorney, Agent, or Firm—David L. Hedden

[57] ABSTRACT

The invention relates to intermediate compounds having the general formula I

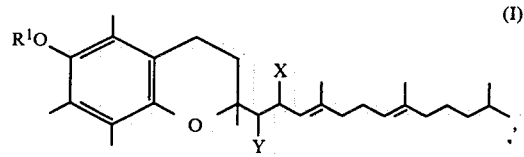

in which $R^1$ is H, an alkyl, arylalkyl or an aliphatic acyl radical, preferably a benzyl or acetyl group and wherein X and Y together span an additional bond between the X and Y carrying C atoms (Ia) or in which Y is OH and X is H (Ib) and in which the dotted line can represent an additional bond particularly

[2R,1'Z,3'E,7'E]-6-benzyloxy-2,5,7,8-tetramethyl-2-(4',8',12'-trimethyl-trideca-1',3',7'-trien-1'-yl)chroman and
6-benzyloxy-2,5,7,8-tetramethyl-2-(1'-hydroxy-4',8',12'-trimethyl-trideca-3',7'-diene-1'-yl)chroman, as well as compounds and methods of preparing compounds having the general formula II

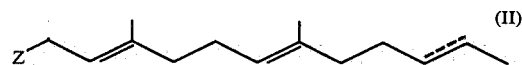

in which Z is one of the groups ClMg—; BrMg—;                                (IIa)

$\oplus(C_6H_5)_3P-$; $Br^{\ominus}(C_6H_5)_3\overset{\oplus}{P}-$            (IIb)

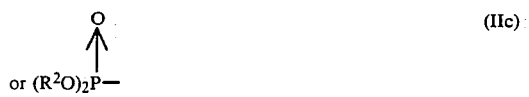

or $(R^2O)_2P-$ wherein $R^2$ is an alkyl group with 1 to 4 carbon atoms preferably $CH_3$ or $C_2H_5$
particularly (3,7,11-trimethyl-trideca-2,6,10-trien-1-yl)triphenylphosphonium chloride and (3,7,11-trimethyl-trideca-2,6,10-trien-1-yl) phosphoric acid dimethylester as well as methods for the preparation of (2R,4'RS,8'Rs)-α-tocopherol and (all-rac)-α-tocopherol via the new intermediate product.

2 Claims, No Drawings

MAGNESIUM CHLORIDE OR PHOSPHONIUM HALIDE DERIVATIVES OF 3,7,11-TRIMETHYL-DODECA-2,6(10)-DIENE(-TRIENE)-1-OL

This is a division, of application Ser. No. 508,802 filed June 28, 1983, now U.S. Pat. No. 4,544,758.

BACKGROUND OF THE INVENTION

1. Field of the Invention

This invention relates to new vitamin E intermediates and methods for their preparation.

2. Prior Art

During the past years, vitamin E ($\alpha$-tocopherol) has gained importance as antioxidant as well as in the field of human and animal nutrition. The most diverse methods are known for synthesizing all-rac-$\alpha$-tocopherol. A survey by Siebrell and Harris on this subject is found in *Vitamins*, vol. V, pages 165 seq, (1972). The more recent literature also contains methods for the preparation of natural, optically active vitamin E (2R,4'R,8'R-$\alpha$-tocopherol) (compare also N. Cohen et al, *Journal of the Americal Chemical Society*, 101 (1979), pages 6710–16). The preparation of stereoisomers of $\alpha$-tocopherol is of interest since the various stereoisomers have a varying biological effect. Among the three asymmetry centers of the natural vitamin E having formula

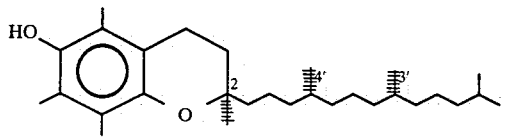

the center at the carbon atom in the 2-position is of particular importance for the biological effect (compare S. Ames, *Lipids* No. 6 (1971), pages 281–290, particularly page 285). Thus, for example, the (2R,4'RS,8'RS), compared with the (2S,4'RS,8'RS) epimer is five times more effective. Because of the multi-stage and complicated nature of the known processes, the synthesis of RRR-$\alpha$-tocopherol appears cumbersome and technically hardly implementable. However, since centers C-4' and C-8' influence the effectiveness of the molecule on a subordinate scale only, a synthesis of (2R,4'RS,8'RS)-$\alpha$-tocopherol is already sufficient to achieve increased biological activity.

In Helv. Chim. Acta, vol. 64; Fasc. 4 (1981), pages 1158–73, Cohen et al describe the preparation of all eight possible stereoisomers of $\alpha$-tocopheryl acetate in high chemical and stereoisomeric purity. The (2R,4'RS,8'RS)isomer was obtained, for example, by reacting racemic tetrahydronerolidol with triphenylphosphonium bromide in $CH_2Cl_2$ and Wittig reaction of the resultant triphenylphosphonium salt with (+)-(S)-6-benzyloxy-2,5,7-tetramethylchroman-2-carbaldehyde in the presence of sodium methylate and subsequent hydrogenation of the resultan $\alpha$-tocopherol on Pd/Charcoal.

SUMMARY OF THE INVENTION

The subject invention relates to compounds having the following general structural formulae:

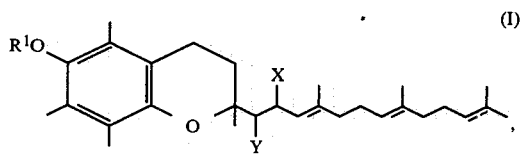

in which $R^1$ is H, an alkyl, arylalkyl or an aliphatic acyl radical, preferably a benzyl or acetyl group, and Y is OH and X is H (Ia) or optionally a compound having an additional bond between the X and Y carrying C atoms (Ib) or optionally a compound having an additional bond at the dotted line; and

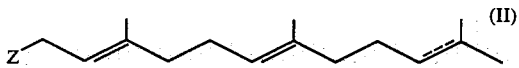

in which Z is one of the groups

ClMg—; BrMg—            (IIa)

            (IIb)

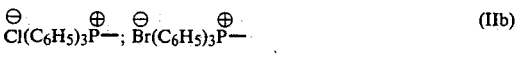            (IIc)

wherein $R^2$ is alkyl of 1 to 4 carbon atoms.

Compounds having formula (I) are prepared by reacting compounds having general formula (II) and one (+)-S-2,5,7-tetramethylchroman-2-carbaldehyde having formula (III):

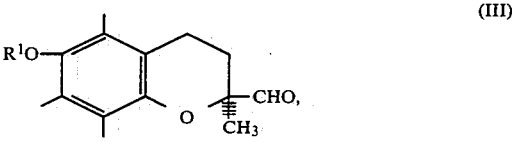

in which $R^1$ is alkyl, arylalkyl or an aliphatic acyl radical.

DETAILED DESCRIPTION OF THE INVENTION

For the practical implementation of the methods according to this invention, the compounds of formula IIb in which Z is

under conditions of a Wittig reaction or compounds of formula IIc in which Z is

under conditions of the variation of the Wittig reaction of Fouquet and Schlosser (compare Angew. Chem., International Edition, 13, (1974) page 82 seq.) are reacted in a basically known manner with a chroman-2-carbaldehyde having formula III to result in the corresponding compound of formula Ib in which X and Y together span an additional bond between the X and Y carrying carbon atoms and wherein this compound is hydrogenated in a basically known fashion using noble metal catalysts such as Pd and activated charcoal to result in (2R,4'RS,8'RS)-α-tocopherol or a 6-O-derivative thereof; or wherein compounds having general formula IIa in which Z stands for Cl-Mg or Br-Mg are reacted under conditions of a Grignard reaction in a basically known manner with a chroman-2-carbaldehyde having formula III to result in the new compounds having formula I in which Y is OH and X is H wherein the corresponding compound of formula I, in which X and Y together span an additional bond, is prepared by dehydration and which compound can then be hydrogenated as described above to result in (2R,4'RS,8'RS)-α-tocopherol or a 6-O-derivative thereof.

By the corresponding reaction of the new compounds of formula II with a 6-O-substituted derivative of the racemic 6-hydroxy-2,5,7,8-tetramethyl-chroman-2-carbaldehyde and subsequent hydrogenation, the corresponding 6-O-derivative of (all-rac)-α-tocopherol can be obtained.

The new compounds having the general formula II can be produced in a basically known fashion from the corresponding halides by reaction with magnesium, triphenylphosphine or trialkylphosphite P(OR$_2$)$_3$.

The reaction of the chroman-(2)-carbaldehydes III and/or IIIa with the organic magnesium halides IIa generally takes place in etheric solvents such as diethylether, tetrahydrofuran (THF), methyl-tertiary-butylether (MTB), dioxane or similar substances.

The water can be separated from the resultant compounds of formula Ia using known substances for dehydration of secondary alcohols such as distillation in the presence of small amounts of an acid, heating with acetic anhydride, or similar substances.

The chroman-(2)-carbaldehydes III and/or IIIa are reacted with the phosphonium salts having formula IIb and/or the phosphonate anions of formula IIc in such a manner that these substances are transformed into the corresponding anions using the bases normally used for this purpose such as alkali hydroxides; metal hydrides, particularly NaH; alkali metal organic compounds, particularly butyl lithium; or ammonium and by reacting these in suitable solvents such as alkanols; ethers, particularly dimethoxyethane, and THF; dimethylformamide, N-methyl-pyrrolidone, dimethylsulfoxide or similar substances at a temperature of −40° C. to 100° C., preferably −10° C. to +80° C. with III and/or IIIa. Compared with the familiar analogous Wittig reaction with a saturated halide, this reaction is more advantageous by the fact that the formation of the phosphonium salt and particularly the anion production is more easily facilitated as a result of the allyl position of the halide radical.

Depending upon the starting materials used, the compounds of formula I resulting from this reaction are obtained in various isomeric forms. When using optically active III, one obtains optially active I. Depending upon the adduct used, the double bonds may be present as E/Z mixtures or in sterically uniform form. Thus, for example, the reaction of III with compounds of IIb in all-E-form results predominantly in the 1'Z,3'E,7'-E,11'E-isomers of Ib.

The compounds of formula I are hydrogenated with the use of catalysts normally applied for olefin hydrogenations such as nobel metals, particularly Pd and Pt or Raney nickel in inert solvents such as alkanols, esters, particularly ethylacetate, under a hydrogen pressure of 1 to 100 bars at a temperature of −10° C. to +150° C., preferably of +10° C. to 100° C.

When using compounds of formula I in which R is a hydrogenolytically cleavable group such as the benzyl group, the α-tocopherol is obtained directly.

The new compounds having the general formulas I and II facilitate advantageous methods for the preparation of (2R,4'RS,8'RS)-α-tocopherol and (all-rac)-α-tocopherol. Furthermore, the compounds of formula I are usable as antioxidants.

The following examples illustrate the various aspects of the invention but are not intended to limit its scope. Where not otherwise specified throughout this specification and claims, temperatures are given in degrees centigrade and parts, percentages and proportions are by weight.

EXAMPLE 1

Preparation of (2R,4'RS,8'RS)-α-tocopherol (a) (2E,6E)-1-chloro-3,7,11-trimethyl-dodeca-2,6-diene:

An amount of 7.70 grams (34.4 mmol) (2E,6E)-3,7,11-trimethyl-dodeca-2,6-dien-1-ol in 54 ml of CH$_2$Cl$_2$ were mixed at room temperature (RT) with 7.18 grams (35 mmol) PCl$_5$ and the reaction mixture was refluxed for one hour. Subsequently, the mixture was mixed with H$_2$O, was extracted with CH$_2$Cl$_2$, was washed with saturated NaHCO$_3$ solution and water and the extract was dried and concentrated. The resulting crude product was distilled in a ball tube (Kugel rohr) over 0.3 gram of solid K$_2$CO$_3$ at 100° C. and a pressure of 0.2 mbar. The result was 5.40 grams (2E, 6E) of 1-chloro-3,7,11-trimethyl-dodeca-2,6-diene in the form of an oil. The yield was 65 percent of theory.

(b) Five grams of the chloride obtained according to (a) and 5.5 grams (21 mmol) of triphenylphosphine were heated to boiling in 15 ml of toluene for five hours. The resultant suspension was stirred with 100 ml of hexane and was decanted therefrom after the white solid substance had settled out. This stirring with hexane was repeated five times, and the remaining tacky solid material was dried under reduced pressure. An amount of 7.2 grams of 2E,6E-(3,7,11-trimethyl-dodeca-2,6-dien-1-yl)triphenylphosphonium chloride was obtained.

(c) Added to a suspension of 4.4 grams (8.3 mmol) of a phosphonium salt produced according to (b) in 35 ml of diethylether were 6.27 ml (1.28 mmol) of butyl lithium in hexane in a dropwise fashion at −10° C., and the reaction mixture was agitated for 10 minutes. Subsequently, 20 ml of dimethylformamide (DMF) were added and 0.92 gram (2.8 mmol) of 2S-6-benzyloxy-2,5,7,8-tetramethyl-chroman-2-carbaldehyde dissolved in 35 ml of diethylether was added dropwise at −10° C. The mixture was then agitated at −10° C. for two hours, was mixed with H$_2$O, extracted with hexane, dried and concentrated. The crude product was chromatographed on 200 grams of silica gel with hexane-ethylacetate (9:1). An amount of 0.86 grams (60 percent of theory) [2S]-6-benzyloxy-2,5,7,8-tetramethyl-2-(4',8',12'-trimethyl-trideca-1',3',7'-trien-1'-yl)chroman was obtained in the form of a colorless oil as a diastereoisomeric mixture. A sample thereof was purified by HPLC in a silica column (Merck Si 60) with i-octane/ethylacetate (99.5:0.5):

$[\alpha]_D^{25} = +43.4(c=1.5/CH_2Cl_2)$.

(d) Hydrogenation to (2R,4'RS,8'RS)-α-tocopherol.

Sixty-one grams of a product obtained in accordance with (c) were hydrogenated with 54 mg Pd/Charcoal (5 percent) in 15 ml of ethylacetate under normal pressure and at room temperature.

After completing the hydrogen absorption, the reaction mixture was filtered, concentrated and distilled in a ball tube (Kugel rohr) at 200° C. and under a pressure of $10^{-2}$ mbar. An amount of 0.32 gram (2R,4'RS,8'RS)-α-tocopherol was obtained as colorless oil. (Yield 52 percent of theory.)

EXAMPLE 2

Preparation of (all-rac)-α-tocopherylacetate (a) (3,7,11-trimethyl-dodeca-2,6,10-trien-1-yl)triphenylphosphonium chloride (E/Z isomer mixture).

An amount of 10.0 grams (41.6 mmol) of Farnesyl chloride and 10.9 grams (41.6 mmol) triphenylphosphine were heated in 30 ml toluene for five hours under reflux. The resultant suspension was stirred with approximately 200 ml hexane and after precipitation of the white solid material was decanted; this stirring process with hexane was repeated five times and the remaining tacky solid substance was dried under reduced pressure.

An amount of 18.2 grams (3,7,11)-trimethyl-dodeca-2,6,10-trien-1-yl)triphenylphosphonium chloride (E/Z isomer mixture) was obtained corresponding with a yield of 87 percent of theory.

(b) Added dropwise to 1.00 gram (1.96 mmol) of the phosphonium salt produced in accordance with (a) in 10 ml of diethyl ether were 1.5 ml (2 mmol) of butyl lithium in hexane at room temperature and the mixture was stirred at room temperature under an argon gas blanket for five minutes. Subsequently a solution of 0.43 grams (1.33 mmol) of rac-6-benzyloxy-2,5,7,8-tetramethyl-chroman-2-carbaldehyde (produced in accordance with N. Cohen et al, *Journal of American Chemical Society*, 101, (1979), pages 6710 seq., particularly page 6715) in 10 ml of diethylether was added to the above-described mixture at −10° C. After standing at room temperature for 30 minutes, the mixture was mixed with 20 ml of absolute dimethylformamide and was stirred for an additional 30 minutes. After adding 10 ml of H₂O, the mixture was extracted with diethylether, the extract was washed, dried and concentrated. The substance was chromatographed on 150 grams of silica gel with toluene/ethylacetate (7:3). An amount of 0.66 gram (97 percent of theory) of 6-benzyloxy-2,5,7,8-tetramethyl-(4',8',12'-trimethyltrideca-1',3',7'11'-tetraen-1'-yl)chroman was obtained.

(c) The crude product obtained according to (b) was hydrogenated in 15 ml of ethylacetate on 0.10 gram of Pd/charcoal (5 percent) under normal pressure and at room temperature for 16 hours. Subsequently the substance was filtered, concentrated and was mixed with 5 ml acetic anhydride and 5 ml of pyridine at 0° to +10° C. After 16 hours at room temperature the mixture was poured into water, extracted with petroleum ether, and washed with dilute hydrochloric acid, saturated NaHCO₃ solution and water, dried and concentrated. An amount of 0.35 gram of (all-rac)-α-tocopherol acetate was obtained as a colorless oil (yield 56 percent of theory).

EXAMPLE 3

(3,7,11-trimethyl-dodeca-2,6-dien-1-yl)triphenylphosphonium chloride (E/Z isomer mixture).

An amount of 9.1 grams (37 mmol) of 1-chloro-3,7,11-trimethyl-dodeca-2,6-diene and 9.8 grams (37 mmol) of triphenyl phosphine were heated to boiling in 30 ml of toluene for a period of five hours. The resultant suspension was mixed with 200 ml of hexane and after precipitation of the white solid material, the liquid was decanted. This mixing with hexane was repeated five times and the remaining tacky solid substance was dried under reduced pressure. An amount of 18.2 grams (3,7,11)-trimethyl-dodeca-2,6,10-trien-1-yl)triphenylphosphonium chloride (E/Z isomer mixture) was obtained. The yield was 87 percent of theory.

EXAMPLE 4

(a) (3,7,11-trimethyl-dodeca-2,6-dien-1-yl)-magnesium chloride (E/Z isomer mixture).

An amount of 1.38 grams (57.5 mmol) of Mg shavings in 120 ml of tetrahydrofuran (THF) were mixed with 5.7 ml of dibromoethane while being stirred and were heated to boiling for 30 minutes. The solvent was removed by distillation and the residue was heated to 150° C. in an argon stream for one hour. After cooling, the mixture was mixed with 80 ml of THF, 3.32 grams (20 mmol) KI and 1.48 grams (37.9 mmol) of potassium pieces and was heated to boiling while being vigorously stirred for three hours. The resultant suspension was agitated at 0° to −5° C. with 14.5 grams (57.9 mmol; approximately 90 percent content) of 1-chloro-3,7,11-trimethyl-dodeca-2,6-diene and was stirred at 0° C. for 15 minutes. The resultant suspension was filtered under argon. The result was 260 ml of a grey solution which had a content of 0.2 mol/l of the Grignard compound (90 percent of theory) after filtration with n-butanol.

(b) To 0.49 gram (1.51 mmol) (rac)-6-benzyloxy-2,5,7,8-tetramethyl-chroman-2-carbaldehyde in 12 ml of THF there were added dropwise, 11.8 ml of a 1.44 molar Grignard solution prepared in accordance with Example 4(a) and the reaction mixture was stirred at room temperature for 14 hours. Subsequently the product was mixed with 20 ml of concentrated NH₄Cl solution, extracted with hexane, washed with H₂O, dried and concentrated. The crude product was chromatographed on 160 grams silica gel with hexane/ethyl acetate (9:1). The result was 0.64 grams of 6-benzyloxy-2,5,7,8-tetramethyl-2-(1'-hydroxy-4',8',12'-trimethyl-trideca-3',7'-dien-1-yl)chroman (diastereoisomer mixture) as a light yellow oil. The yield was 80 percent of theory.

EXAMPLE 5

(a) (3,7,11-trimethyl-dodeca-2,6-dien-1-yl)phosphorous dimethylester.

An amount of 30 grams (125 mmol) E/Z-Farnesyl chloride and 15.5 grams (125 mmol) phosphorous trimethylester were heated to boiling under reflux for five hours. Subsequently the mixture was distilled at a pressure of 0.2 mbar and 150° C. to 170° C. The result was 15.6 grams (3,7,11-trimethyl-dodeca-1,6-dien-1-yl)phosphorous dimethylester as a pale yellow oil. The yield was 40 percent (not optimized).

(b) An amount of 0.60 gram (1.9 mmol) of a phosphorous ester obtained in accordance with Example 5(a) was dissolved in 5 ml dimethylsulfoxide (DMSO) and mixed with 50 mg of 80 percent NaH in mineral oil, and the mixture was stirred at room temperature for one hour. Subsequently, 0.50 gram (1.5 mmol) of (rac)-6-benzyloxy-2,5,7,8-tetramethyl-chroman-2-carbaldehyde in 3 ml of DMSO were added and the reaction mixture was allowed to stand for 16 hours. After this period, the substance was diluted with approximately 100 ml of diethylether, was washed with water four times, dried and concentrated. The result was 0.51 gram of crude product which was chromatographed on 30 grams of silica gel with diethylether/hexane (1:8). An amount of 0.27 gram of 6-benzyloxy-2,5,7,8-tetramethyl-2-(4′,8′,12′-trimethyl-trideca-1′,2′,6′,10′-tetra-en-1′-yl)chroman was obtained as colorless oil (diastereo isomer mixtures).

EXAMPLE 6

Analogous with Example 4(a), 200 ml of a Grignard solution were obtained from 1.0 gram (41.7 mmol) of Mg shavings and 12.0 grams (42 mmol) of 1-bromo-3,7,11-trimethyl-dodeca-2,6,10-triene which contained 1.67 moles per liter of 3,7,11-trimethyl-dodeca-2,6,10-triene-1-yl)magnesium bromide (E/Z isomer mixture). The yield thus is approximately 80 percent of theory.

While this invention has been described with reference to certain specific embodiments, it will be recognized by those skilled in the art that many variations are possible without departing from the scope and spirit of the invention and it will be understood that it is intended to cover all changes and modifications of the invention disclosed herein for the purposes of illustration which do not constitute departures from the spirit and scope of the invention.

The embodiments of the invention in which an exclusive property or privilege is claimed are defined as follows:

1. A compound having the general formula II

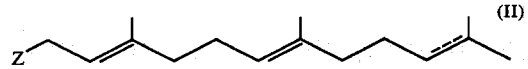

wherein the dotted line indicates that the compound may have an additional double bond at the 11 position, and in which Z is one of the groups

2. (3,7,11-trimethyl-trideca-2,6,10-trien-1-yl)triphenylphosphonium chloride.

* * * * *